United States Patent
Seykora et al.

(10) Patent No.: US 12,048,440 B2
(45) Date of Patent: Jul. 30, 2024

(54) ORTHOPEDIC REAMER WITH EXPANDABLE CUTTING HEAD

(71) Applicant: Acumed LLC, Hillsboro, OR (US)

(72) Inventors: Andrew William Seykora, Portland, OR (US); Brian R. Conley, Portland, OR (US); Larry W. Ehmke, Portland, OR (US); Brent Lane Norris, Jenks, OK (US); Alexander William Huettis, Aloha, OR (US); Gregory D. Hutton, Beaverton, OR (US)

(73) Assignee: Acumed LLC, Hillsboro, OR (US)

( * ) Notice: Subject to any disclaimer, the term of this patent is extended or adjusted under 35 U.S.C. 154(b) by 220 days.

(21) Appl. No.: 17/555,935

(22) Filed: Dec. 20, 2021

(65) Prior Publication Data

US 2022/0110638 A1    Apr. 14, 2022

Related U.S. Application Data

(63) Continuation of application No. 16/001,867, filed on Jun. 6, 2018, now Pat. No. 11,219,466.

(51) Int. Cl.
*A61B 17/16* (2006.01)
*A61B 17/00* (2006.01)
*A61B 90/00* (2016.01)

(52) U.S. Cl.
CPC ........ *A61B 17/164* (2013.01); *A61B 17/1617* (2013.01); *A61B 17/1622* (2013.01);
(Continued)

(58) Field of Classification Search
CPC ........ A61B 17/164; A61B 2017/00867; A61B 17/1717; A61B 17/1642; A61B 17/1631; A61B 17/320725; A61B 90/06
See application file for complete search history.

(56) References Cited

U.S. PATENT DOCUMENTS 4,357,846 A * 11/1982 Primo .................. B23B 5/40
                                                   82/1.4
4,706,659 A    11/1987 Matthews et al.
(Continued)

FOREIGN PATENT DOCUMENTS

AU    2004203352 A1    8/2004
AU    2004203352 B2    8/2007
(Continued)

OTHER PUBLICATIONS

Biomedical Enterprises, Inc., BoneHOG(TM) Surgical brochure, date unknown, 21 pgs.
(Continued)

*Primary Examiner* — David W Bates
(74) *Attorney, Agent, or Firm* — K&L Gates LLP

(57) ABSTRACT

Device and method for reaming bone. In exemplary embodiments, the device may comprise a shaft configured to be rotated about a long axis thereof. The device also may comprise a plurality of cutting members connected to a distal end region of the shaft, rotationally offset from one another about the long axis, and forming a portion of an expandable cutting head. The device further may comprise an inner member configured to be moved with respect to the shaft to change a diameter of the cutting head. In exemplary methods, the device may be utilized to ream a medullary cavity while being pushed or pulled along the medullary cavity.

20 Claims, 9 Drawing Sheets

(52) U.S. Cl.
CPC ..... *A61B 17/1631* (2013.01); *A61B 2017/00367* (2013.01); *A61B 2017/00477* (2013.01); *A61B 2090/0811* (2016.02)

(56) References Cited

U.S. PATENT DOCUMENTS

| | | | |
|---|---|---|---|
| 4,751,922 A | 6/1988 | DiPietropolo | |
| 4,992,010 A * | 2/1991 | Fischer | B23B 51/0045 175/286 |
| 5,122,134 A * | 6/1992 | Borzone | A61B 17/164 407/30 |
| 5,275,610 A | 1/1994 | Eberach | |
| 5,509,919 A | 4/1996 | Young | |
| 5,591,170 A * | 1/1997 | Spievack | A61B 17/142 606/177 |
| 6,070,677 A | 6/2000 | Johnston, Jr. | |
| 6,224,604 B1 | 5/2001 | Suddaby | |
| 6,447,518 B1 | 9/2002 | Krause et al. | |
| 6,676,665 B2 | 1/2004 | Foley et al. | |
| 6,783,533 B2 | 8/2004 | Green et al. | |
| 7,429,264 B2 | 9/2008 | Melkent et al. | |
| 8,114,084 B2 | 2/2012 | Betts | |
| 8,961,518 B2 | 2/2015 | Taylor et al. | |
| 9,282,980 B2 | 3/2016 | O'Neil et al. | |
| 9,381,031 B2 | 7/2016 | Rains et al. | |
| 9,603,607 B2 | 3/2017 | Papenfuss | |
| 10,448,959 B2 | 10/2019 | Slobitker et al. | |
| 11,357,517 B1 * | 6/2022 | Amin | A61B 17/1675 |
| 2001/0034526 A1 | 10/2001 | Kuslich et al. | |
| 2005/0113836 A1 * | 5/2005 | Lozier | A61B 17/1617 606/80 |
| 2006/0025774 A1 | 2/2006 | Fishbein et al. | |
| 2006/0241629 A1 * | 10/2006 | Krebs | A61B 17/1668 606/80 |
| 2006/0264952 A1 * | 11/2006 | Nelson | A61B 17/7275 606/62 |
| 2007/0060933 A1 | 3/2007 | Sankaran et al. | |
| 2007/0276392 A1 | 11/2007 | Beyar et al. | |
| 2008/0114364 A1 * | 5/2008 | Goldin | A61B 17/1617 606/170 |
| 2008/0161805 A1 * | 7/2008 | Saravia | A61B 17/7266 606/60 |
| 2008/0228208 A1 | 9/2008 | Wulfman et al. | |
| 2008/0275448 A1 | 11/2008 | Sackett et al. | |
| 2008/0275449 A1 | 11/2008 | Sackett et al. | |
| 2009/0182336 A1 * | 7/2009 | Brenzel | A61B 17/869 606/62 |
| 2009/0281545 A1 * | 11/2009 | Stubbs | A61F 2/32 623/22.21 |
| 2010/0249785 A1 | 9/2010 | Betts | |
| 2011/0251616 A1 * | 10/2011 | Osman | A61B 17/1671 606/80 |
| 2011/0306975 A1 | 12/2011 | Kaikkonen et al. | |
| 2012/0179161 A1 * | 7/2012 | Rains | A61B 17/1617 606/80 |
| 2013/0018376 A1 | 1/2013 | Yoon et al. | |
| 2013/0165935 A1 * | 6/2013 | Griffiths | A61B 17/1617 606/80 |
| 2014/0155899 A1 * | 6/2014 | Bowman | A61B 17/1617 606/80 |
| 2014/0257297 A1 * | 9/2014 | Koogle, Jr. | A61B 17/1668 606/80 |
| 2014/0276844 A1 * | 9/2014 | Bourque | A61B 17/1631 606/80 |
| 2014/0336653 A1 | 11/2014 | Bromer | |
| 2015/0190147 A1 * | 7/2015 | Ferragamo | A61B 17/1675 606/80 |
| 2015/0265287 A1 * | 9/2015 | Berberich | A61B 17/1615 606/80 |
| 2015/0282817 A1 | 10/2015 | Osman et al. | |
| 2016/0038157 A1 * | 2/2016 | Mirochinik | A61B 17/1796 606/80 |

FOREIGN PATENT DOCUMENTS

| | | |
|---|---|---|
| DE | 3840466 A1 | 6/1990 |
| EP | 1148825 B1 | 3/2005 |
| EP | 2928389 A1 | 10/2015 |
| JP | 2005152650 A | 6/2005 |
| JP | 2015536736 A | 12/2015 |

OTHER PUBLICATIONS

Depuy Synthes, "Reamer/Irrigator/Aspirator (RIA)", Surgical Technique, (c) 2015, 36 pgs.
Stryker, "T2(TM) Femoral Nailing System Operative Technique", Howmedica Osteonics, (c) 2005, 42 pgs.
Thomas, Shane, Authorized Officer, ISA/US, Commissioner for Patents, "International Search Report" in connection with related International Application No. PCT/US2019/035522, dated Aug. 29, 2019, 2 pgs.
Thomas, Shane, Authorized Officer, ISA/US, Commissioner for Patents, "Written Opinion of the International Searching Authority" in connection with related International Application No. PCT/US2019/035522, dated Aug. 29, 2019, 10 pgs.
Extended European Search Report corresponding to related European Application No. 19814141.8, mailed May 20, 2022, 10 pages.
Japanese Office Action corresponding to Japanese Application No. 2020-567006; report dated Dec. 24, 2021; (15 pages).

* cited by examiner

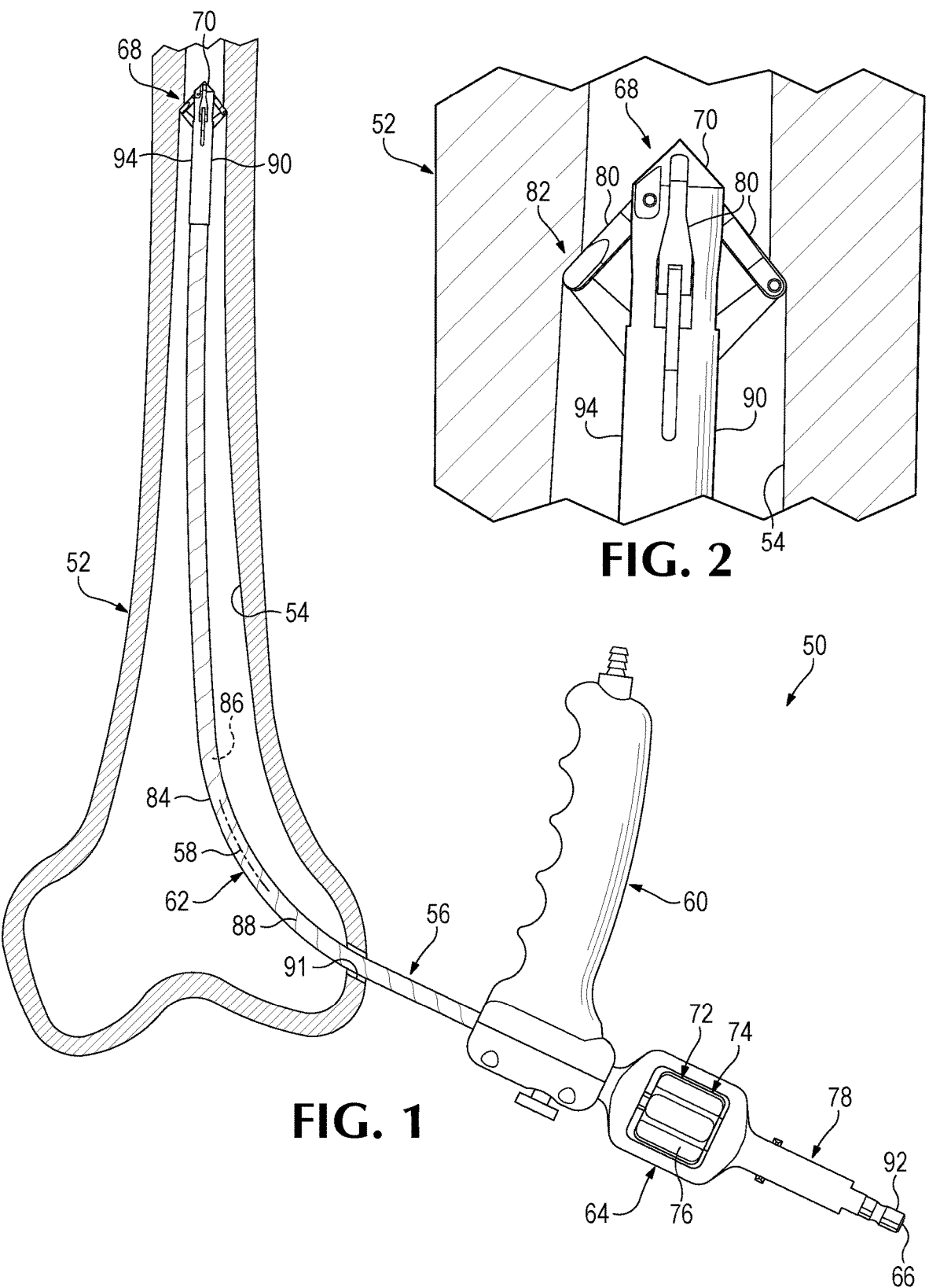

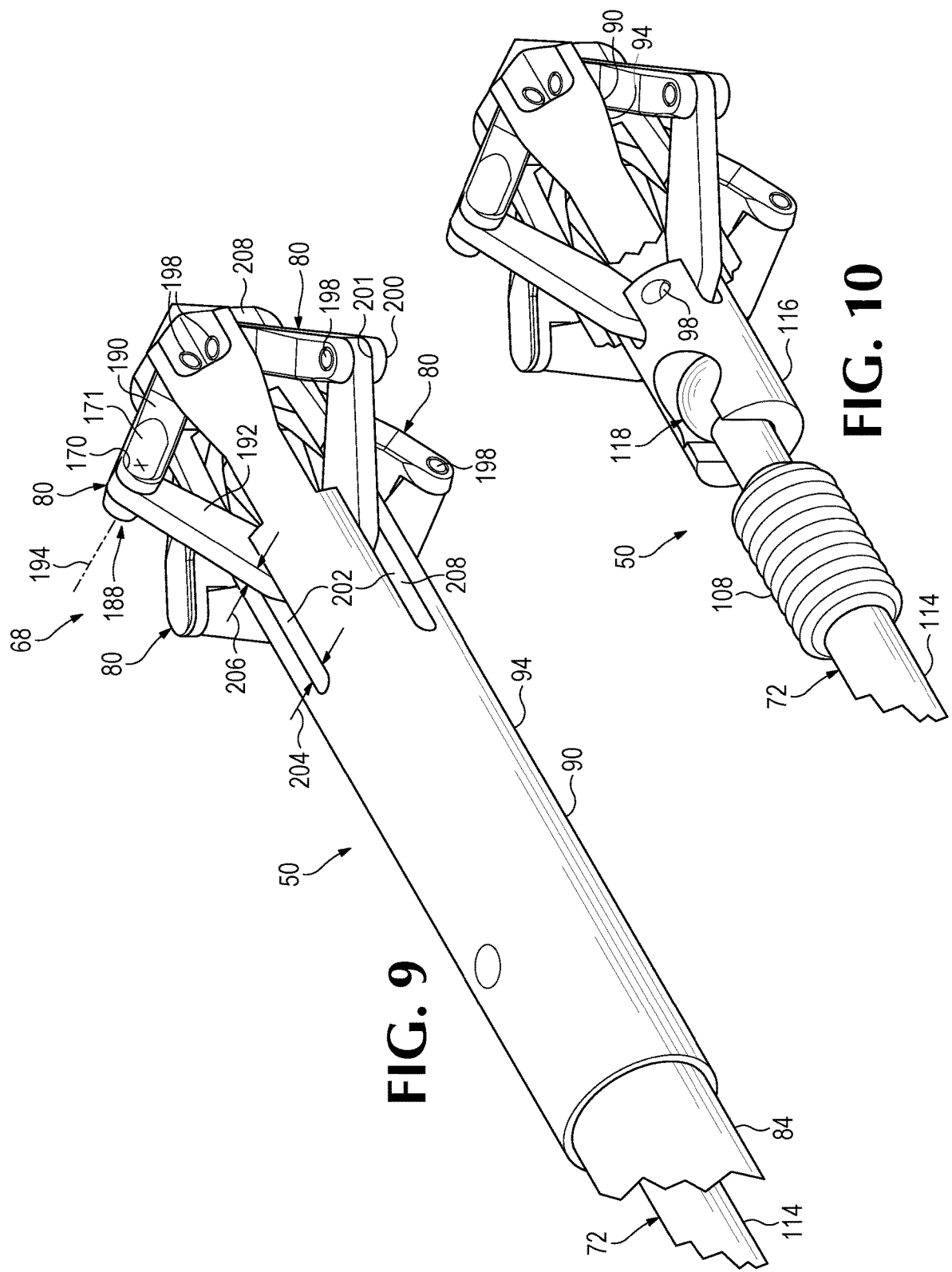

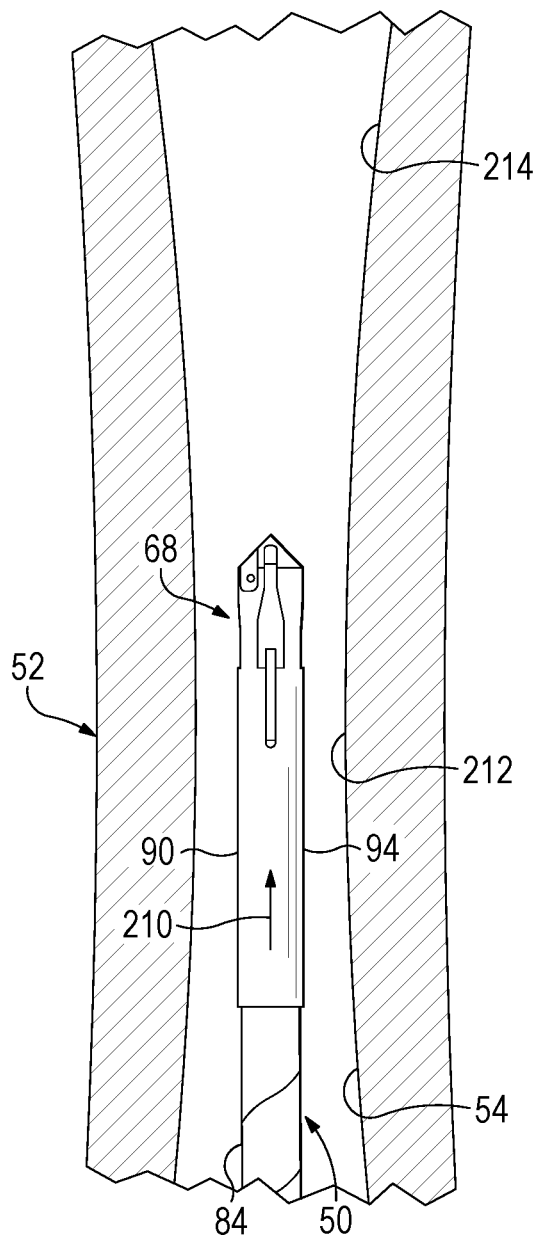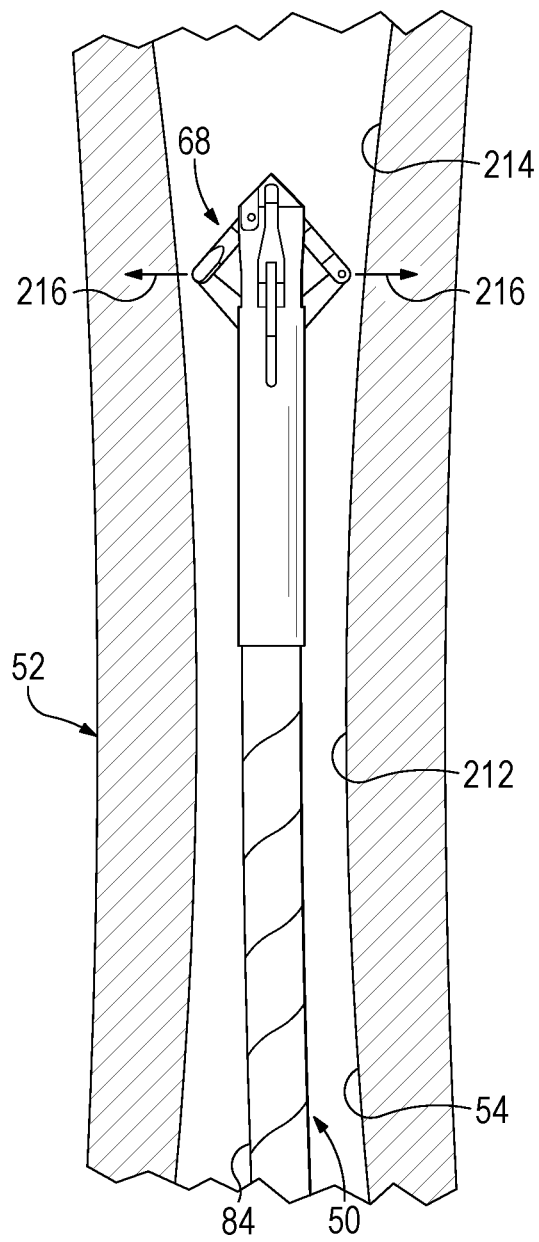

US 12,048,440 B2

ORTHOPEDIC REAMER WITH EXPANDABLE CUTTING HEAD

PRIORITY CLAIM

The present application is a continuation of U.S. application Ser. No. 16/001,867, filed Jun. 6, 2018, the entire contents of which are incorporated herein by reference and relied upon.

INTRODUCTION

An orthopedic reamer is a surgical tool to widen a cavity in bone. The reamer may be utilized to cut cortical bone from the wall of a long bone's medullary cavity to prepare the bone to receive an intramedullary nail. In a typical reaming procedure before nail installation, a surgeon advances a series of reamer heads of increasing diameter along a medullary cavity until one of the reamer heads meets sufficient resistance. This procedure creates a reamed cavity having a defined minimum diameter, to provide a snug fit for a correspondingly-sized nail. However, the procedure is time consuming and requires formation of a large opening on the bone through which each reamer head can enter the medullary cavity.

Orthopedic reamers equipped with an expandable cutting head have been disclosed. However, these reamers are not sturdy enough to ream cortical bone, cannot be bent sufficiently during use, and/or do not accurately report, outside bone, the current size of the reamer's cutting head inside bone. A new orthopedic reamer with an expandable cutting head and methods of using the reamer to ream a medullary cavity are needed.

SUMMARY

The present disclosure provides a device and method for reaming bone. In exemplary embodiments, the device may comprise a shaft configured to be rotated about a long axis thereof. The device also may comprise a plurality of cutting members connected to a distal end region of the shaft, rotationally offset from one another about the long axis, and forming a portion of an expandable cutting head. The device further may comprise an inner member configured to be moved with respect to the shaft to change a diameter of the cutting head. In exemplary methods, the device may be utilized to ream a medullary cavity while being pushed or pulled along the medullary cavity.

BRIEF DESCRIPTION OF THE DRAWINGS

FIG. 1 is a fragmentary, sectional view of a portion of the cortex of a femur being push-reamed with an exemplary reamer having a flexible shaft and an expandable cutting head, in accordance with aspects of the present disclosure.

FIG. 2 is magnified view of an area of FIG. 1 taken around the expandable cutting head.

FIG. 9 is a fragmentary, non-sectional view of the distal end region of the reamer of FIG. 1, taken with the cutting head expanded as in FIG. 8.

FIG. 10 is another fragmentary, non-sectional view of the distal end region of the reamer of FIG. 1, taken generally as in FIG. 9 except showing a shorter portion of the distal end region and omitting most of the reamer's shaft.

FIGS. 12-15 are fragmentary, sectional views of the cortex of a femur taken during performance of a pull-reaming method using the reamer of FIG. 1.

DETAILED DESCRIPTION

Figure 3:
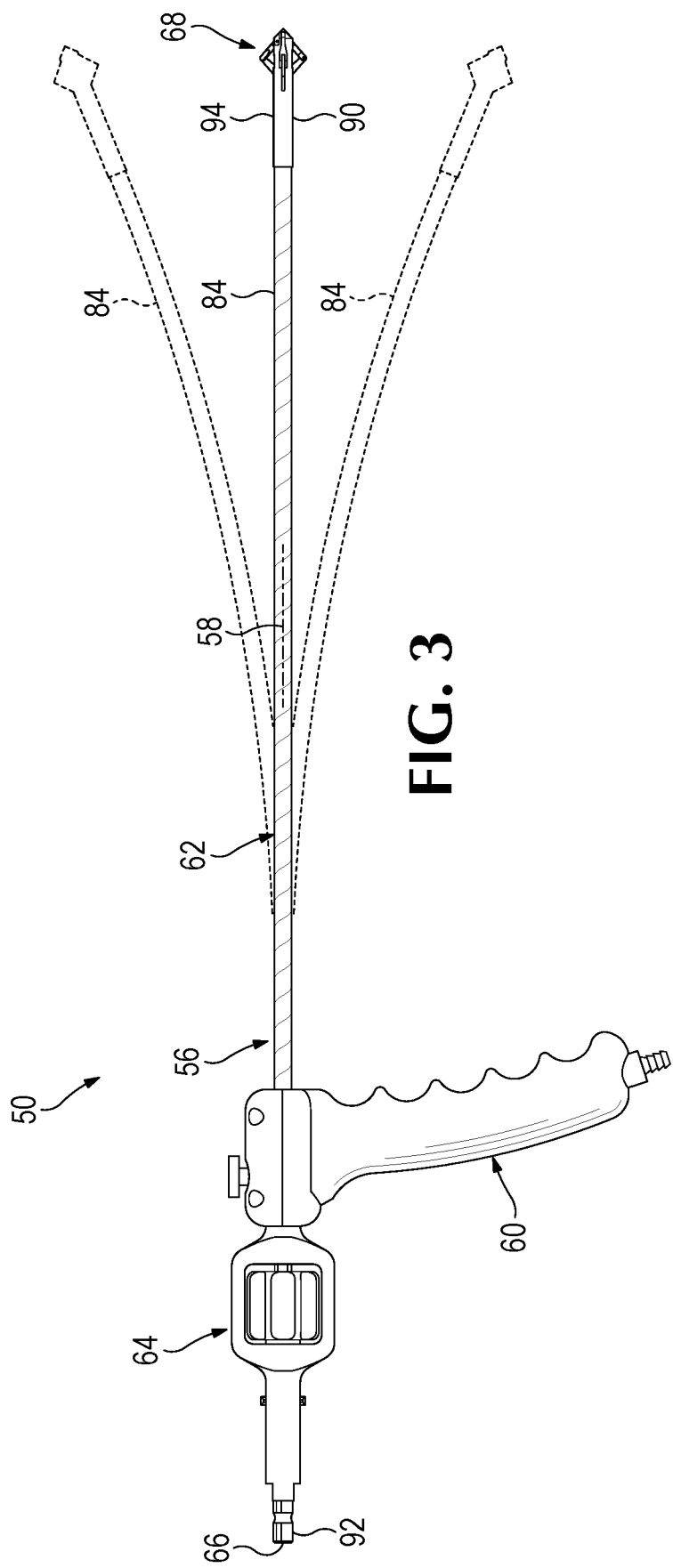
FIG. 3 is a side view of the reamer of FIG. 1, with exemplary bent configurations of the reamer's shaft illustrated in dashed outline.

The present disclosure provides a device and method for reaming bone. In exemplary embodiments, the device may comprise a shaft configured to be rotated about a long axis thereof. The device also may comprise a plurality of cutting members connected to a distal end region of the shaft and rotationally offset from one another about the long axis. The cutting members may form a portion of an expandable cutting head that is incrementally adjustable to a plurality of different diameters.

In some embodiments, the device also may comprise an inner member, such as a rod, disposed in threaded engagement with the distal end region of the shaft. The inner member may be configured to be rotated about the long axis of the shaft to change a diameter of the cutting head. Distal threaded engagement of the inner member with the shaft ensures that the diameter of the cutting head remains fixed during reaming, and is not affected by bending the shaft or driving rotation of the cutting head with the shaft. The shaft may be flexible, which may allow small changes to the axial separation ("axial slop") and rotational orientation ("rotational slop") of the shaft's opposite ends. The distal threaded engagement disclosed herein can rigidly maintain the diameter of the cutting head in the presence of this axial and rotational slop.

In some embodiments, the device also may comprise a graspable member and a carriage. The shaft may include a flexible sleeve and may be configured to be rotated with respect to the graspable member about the long axis of the shaft. The carriage may be configured to slide axially inside the shaft. Each cutting member may have a first segment and a second segment pivotably connected to one another at a joint. One end of the cutting member may be pivotably connected to the shaft and an opposite end of the cutting member may be pivotably connected to the carriage. An inner member, such as a rod, may extend longitudinally in the sleeve. The inner member may be configured to be rotated with respect to the shaft to drive translational motion of the carriage along the long axis, such that a diameter of the cutting head changes.

In some embodiments, each cutting member may have a first segment and a second segment that are discrete from one another and the shaft, and pivotably connected to one another at a joint. An inner member, such as a rod, may extend along the long axis inside the shaft. The inner member may be configured to be rotated with respect to the shaft by a user such that a distance between the joint and the long axis of the shaft changes.

The device may be utilized to ream a medullary cavity while being pushed or pulled along the medullary cavity. In an exemplary method of pull-reaming, a cutting head of the device may be placed into a medullary cavity of a bone. The cutting head may be advanced through a narrower region to a wider region of the medullary cavity. The cutting head may be expanded in the wider region. The expanded cutting head may be pulled back through the narrower region as the cutting head is rotated, such that the cutting head widens the narrower region.

In some embodiments of the reaming methods disclosed herein, the cutting head may be placed into the medullary cavity via an opening formed in the bone. The diameter of the cutting head may be less than the diameter of the opening while the cutting head is advanced into the cavity through the opening. The cutting head may be expanded inside the medullary cavity to a diameter greater than the diameter of the opening. The expanded cutting head may ream the wall of the medullary cavity. The cutting head may be contracted to a diameter less than the diameter of the opening, and then removed via the opening while in this contracted configuration. This procedure is less damaging to the bone because the medullary cavity can be accessed through a smaller opening.

In some embodiments, the device may be utilized to measure a local diameter of the medullary cavity of a bone. The cutting head may be disposed at a desired longitudinal position along the medullary cavity, such as at the isthmus thereof. The longitudinal position may be selected or confirmed via radiographic imaging. The cutting head may be expanded until contact between the cutting head and the wall of the medullary cavity produces a detectable resistance to further expansion. The resistance may be detected by haptic feedback (i.e., by feel). The size of the cutting head then may be read by the user from a gauge of the device located outside bone.

The reaming device and methods of the present disclosure may offer various advantages for reaming bone of a subject, including any combination of the following. The reaming device may have a sturdy cutting head, which may allow the device to cut cortical bone from the wall of a medullary cavity. The shaft of the reaming device may be configured to be quite flexible without sacrificing reliable measurement of the diameter of the cutting head of the device. A user may adjust the diameter of the cutting head while the cutting head is inside bone, and read the current diameter of the cutting head from a gauge located outside bone. This design permits the cutting head, while contracted, to be placed into a medullary cavity through a smaller hole in bone, and then expanded inside the medullary cavity. Moreover, the local diameter of the medullary cavity adjacent the cutting head can be measured more accurately by expanding the cutting head until it contacts the cavity wall. The expanded cutting head then can be pushed or pulled through the isthmus of the medullary cavity. In some embodiments, pulling the cutting head while cutting bone may provide more efficient force transmission, particularly when the shaft is very flexible. Pushing the cutting head tends to increase the pressure inside the medullary cavity, which can release fat and bone marrow into the venous blood system with potentially lethal consequences. In contrast to push-reaming, the pull-reaming methods disclosed herein may be significantly safer because the intramedullary pressure is reduced. Furthermore, the flexibility of the shaft may allow the cutting head to enter the medullary cavity obliquely to the long axis of the cavity, from an entry site on the bone that is more convenient to the user and/or less invasive for the subject.

Further aspects of the present disclosure are described in the following sections: (I) expandable reamer, (II) methods of reaming bone, and (III) selected embodiments.

I. Expandable Reamer

This section describes an exemplary expandable reaming device or reamer 50; see FIGS. 1-11.

FIGS. 1 and 2 schematically show the cortex of an exemplary long bone, a femur 52, being push-reamed along its medullary cavity 54 with reamer 50. The reamer may include a shaft 56 configured to be rotated about a long axis 58 thereof. Shaft 56 may be rotated with respect to a graspable member 60, which may include a graspable handle portion. The shaft may include a flexible distal portion 62 configured to enter a bone, and a proximal portion 64 configured to remain outside the bone. The terms "proximal" and "distal" as used herein to describe portions, components, and features of reamer 50 generally denote relative proximity to a trailing end 66 of shaft 56, with proximal being closer than distal to trailing end 66. The terms "trailing" and "leading" are used herein as respective synonyms for "proximal" and "distal."

An expandable cutting head 68 may be located near a leading end 70 of shaft 56. Cutting head 68 may be expanded, to increase its diameter, or contracted, to decrease its diameter, using an actuator 72. The actuator may be manipulated via a user interface 74 (e.g., a knob 76) that is connected to and supported by proximal portion 64 of shaft 56. The diameter of cutting head 68 may be indicated by a gauge 78 that is coupled to actuator 72. Gauge 78 may be located proximally in reamer 50, such as more proximally than user interface 74, as shown here, or vice versa. The diameter of cutting head 68 is a rotary diameter, namely, the diameter of a solid of revolution representing the volume of the cutting head integrated over a full revolution about long axis 58. More simply, the (current) diameter may be defined as twice the current maximum radius of the cutting head measured orthogonally with respect to long axis 58.

Cutting head 68 may be formed in part by a section of shaft 56 and in part by a plurality of cutting members 80 each coupled to the section of the shaft (see FIG. 2). The cutting members are configured to cut bone, such as cortical bone 82 near cavity 54. Cutting head 68 may have at least one, two, three, or four cutting members 80, among others. However, in some embodiments, cutting head 68 may ream more smoothly, with less chatter, when equipped with at least three cutting members 80. The plurality of cutting members 80 may be rotationally offset from one another about long axis 58, optionally by 360/n degrees, where n is the number of cutting members. For example, the cutting head may have only two cutting members 80, which may be offset by 180 degrees, only three cutting members 80, which may be offset by 120 degrees, only four cutting members 80, which may be offset by 90 degrees (as in the depicted embodiment), or the like.

Shaft 56 may include a flexible sleeve 84 that allows the shaft to bend, optionally elastically (e.g., see FIGS. 1 and 3). The sleeve defines a longitudinal channel 86 in which an elongate portion of actuator 72 may be housed, as described further below. The flexibility of sleeve 84 may be created by a plurality of discrete sleeve segments arranged along long axis 58 and/or by at least one slit 88, such as a generally helical slit, that extends around long axis 58 multiple times (e.g., at least three times, as in the depicted embodiment). The sleeve may be formed by cutting (e.g., laser-cutting) a single slit 88 through the wall of a tube, between a lateral periphery and channel 86 of the tube. Alternatively, the sleeve may be formed by cutting (e.g., laser-cutting) the tube into a series of discrete segments, which may interlock with one another. In other embodiments, the sleeve may be formed by additive manufacturing (e.g., 3D printing).

Sleeve 84 may have any suitable length and flexibility. The sleeve may extend along a majority of the total length of shaft 56 and/or a majority of the total length of distal portion 62 of shaft 56. For example, sleeve 84 may extend along at least about 60%, 70%, 80%, or 90%, among others, of the total length of shaft 56 and/or distal portion 62. The sleeve may be responsible for most of the flexibility of shaft 56, and thus may be more flexible than proximal portion 64 of shaft 56 and/or a distal support member 90 of shaft 56, if present. Distal support member 90 may be mounted firmly to a distal end of sleeve 84, such as via threaded engagement (e.g., see FIG. 6), bonding, a fastener(s), and/or the like. The support member may be elongated along long axis 58 distally from sleeve 84, and may form leading end 70 of shaft 56.

Shaft 56 may be sufficiently flexible to allow reamer 50 to be operated with any suitable amount of introduced bend during a surgical procedure, such as at least about 20, 30, 40, 50, 60, 90, 120, 150, or 180 degrees, among others. Long axis 58 follows shaft 56 longitudinally, whether the shaft is in an unbent configuration (e.g., the shaft is linear) or in a bent configuration (e.g., as in FIG. 1). Accordingly, long axis 58 may be linear, curved, or a combination thereof (e.g., see FIG. 3). The shaft may be sufficiently flexible to accommodate multiple bends simultaneously at different positions along the shaft. For example, the shaft may be bent to be sigmoidal (S-shaped) during use.

The flexibility of shaft 56 may permit cutting head 68 to follow medullary cavity 54 longitudinally even after entry from a side instead of an end of the bone. For example, FIG. 1 shows an access hole 91 formed in a lateral surface region of femur 52. Access hole 91 can be relatively small, because cutting head 68 can pass through access hole 91 while each of cutting members 80 is in a retracted configuration. Once inside medullary cavity 54, cutting head 68 can be expanded a desired amount to deploy cutting members 80. After reaming medullary cavity 54, cutting members 80 can be retracted to permit withdrawal of cutting head 68 from the bone at access hole 91.

Shaft 56 may form a drive structure 92 near trailing end 66. The drive structure may be configured to be gripped by a driver (e.g., via a collet thereof), which may be a power driver or a manually-operated driver. Torque applied to drive structure 92 by the driver may rotate shaft 56 (and thus cutting head 68) as a unit about long axis 58.

Figure 4:
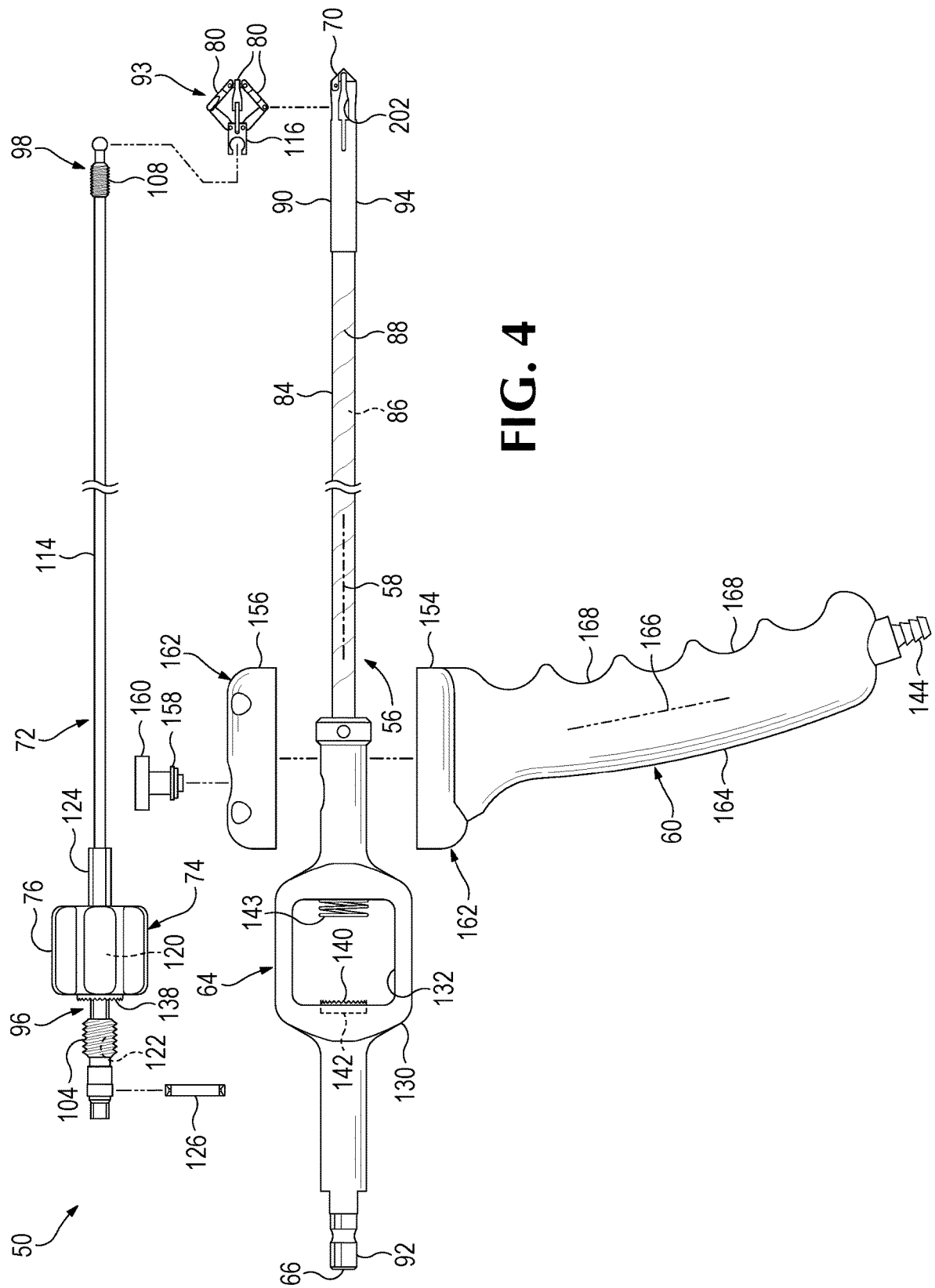
FIG. 4 is an exploded view of the reamer of FIG. 1.

FIG. 4 shows various assemblies and components of reamer 50 separated from one another. Actuator 72 is depicted at the top and shaft 56 in the middle. Graspable member 60 is exploded from shaft 56. An adjustable portion 93 of cutting head 68 is uncoupled from a distal end region 94 of shaft 56 that forms a supporting portion of the cutting head.

Actuator 72 may be configured to be rotated as a unit about long axis 58. The actuator may be elongated between a proximal end portion 96 and a distal end portion 98. One or both end portions 96, 98 may be disposed in threaded engagement with shaft 56 to form respective proximal and distal threaded connections 100, 102 (also see FIGS. 5 and 6). Proximal end portion 96 may include a proximal threaded member, such as a gauge screw 104 having an external thread, for threaded engagement with a complementary shaft thread 106, which may be an internal thread, formed by proximal portion 64 of shaft 56. Distal end portion 98 of actuator 72 may include an external thread 108 that engages an internal thread 110 formed inside distal end region 94 of shaft 56. Distal end region 94 is formed by distal support member 90 in the depicted embodiment.

Figure 6:
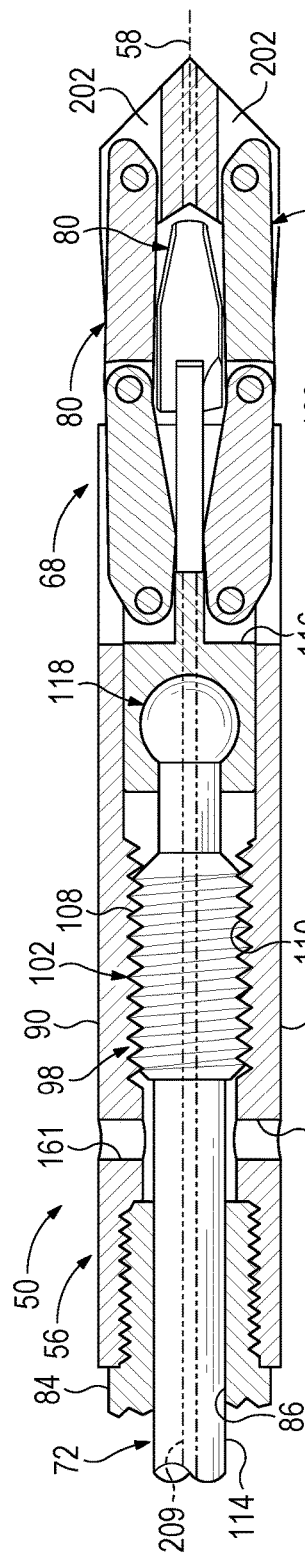
FIGS. 6-8 are fragmentary, sectional views of a distal end region of the reamer of FIG. 1 taken with the cutting head contracted, partially expanded, and fully expanded, respectively.

External thread 108 may be provided by an elongated inner member 114, such as a rod, of actuator 92 (see FIGS. 3 and 6). The inner member may be formed unitarily (as a single, discrete piece) or as two or more discrete pieces that are coupled to one another (e.g., firmly or slidably attached to one another). Inner member 114 may interface with a carriage 116 of cutting head 68 distally. More particularly, the inner member may be rotatable about long axis 58 with respect to carriage 116. For example, inner member 114 and carriage 116 may form a spherical interface 118 (e.g., a ball-in-socket connection) (see FIG. 6). Threaded travel of inner member 114 along long axis 58, driven by rotation of the inner member, may drive translational motion of carriage 116 along axis 58 in distal end region 94 of shaft 56. This translational motion of carriage 116 changes the degree of deployment of cutting members 80 and thus the diameter of cutting head 68 (compare FIGS. 6-8).

Figure 5:
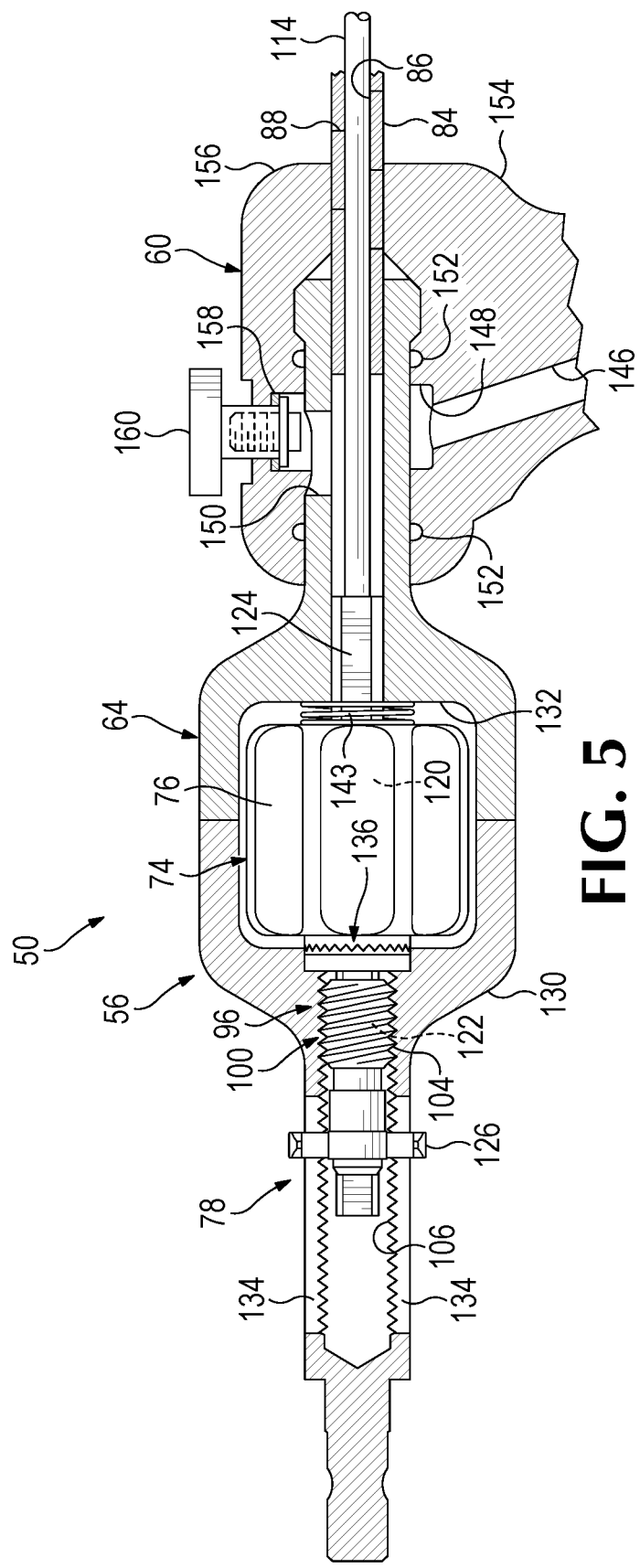
FIG. 5 is a fragmentary, sectional view of a proximal portion of the reamer of FIG. 1, sectioned along a central plane of the reamer parallel to the view of FIG. 3.
Figure 11:
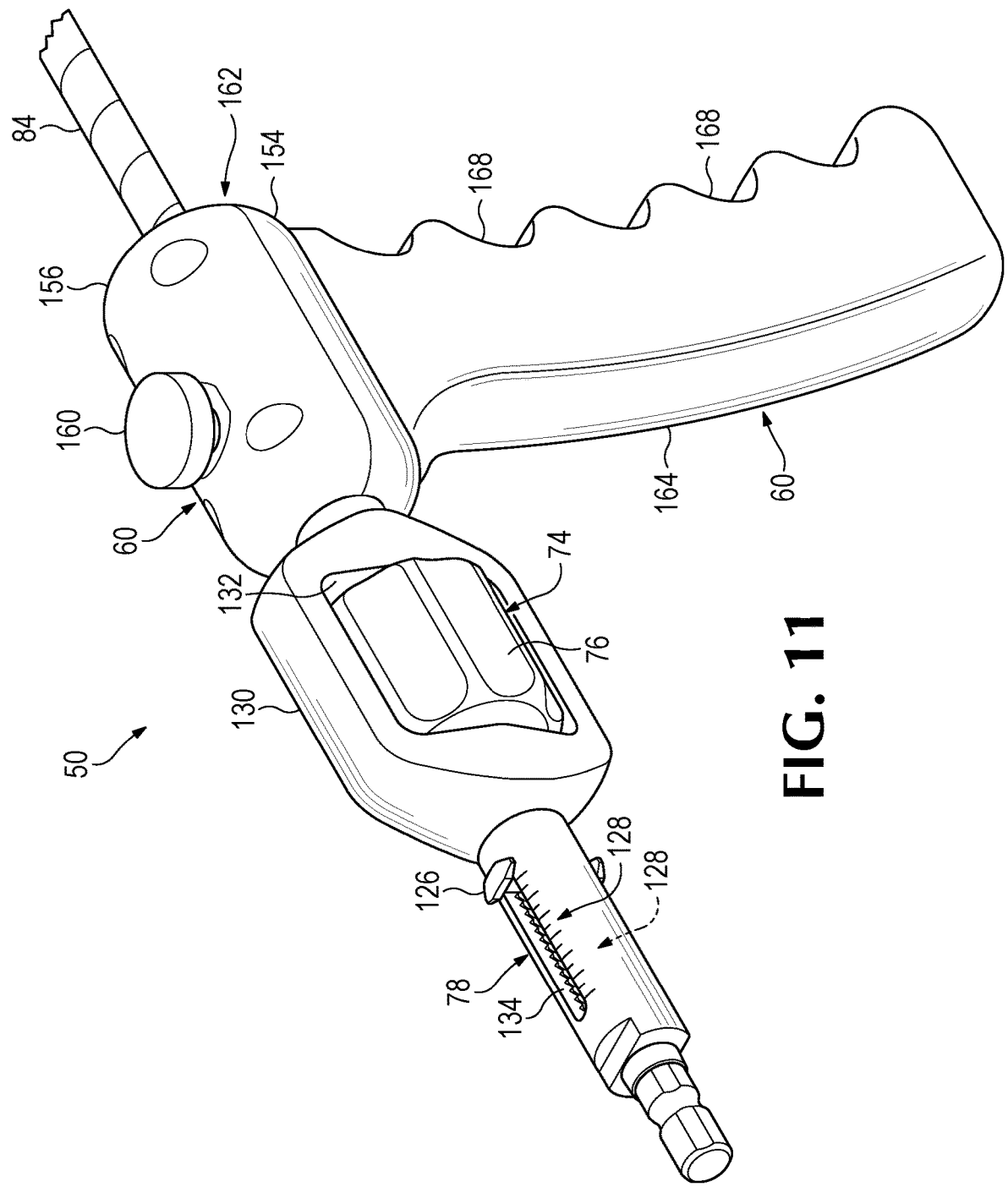
FIG. 11 is a fragmentary view of the reamer of FIG. 1 taken around the proximal portion of the reamer.
Figure 14:
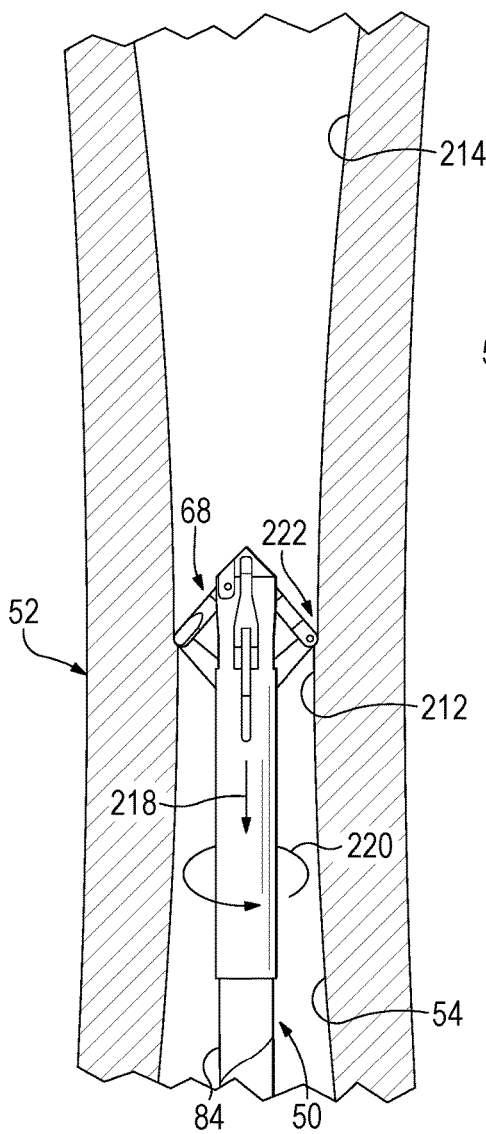
Figure 15:
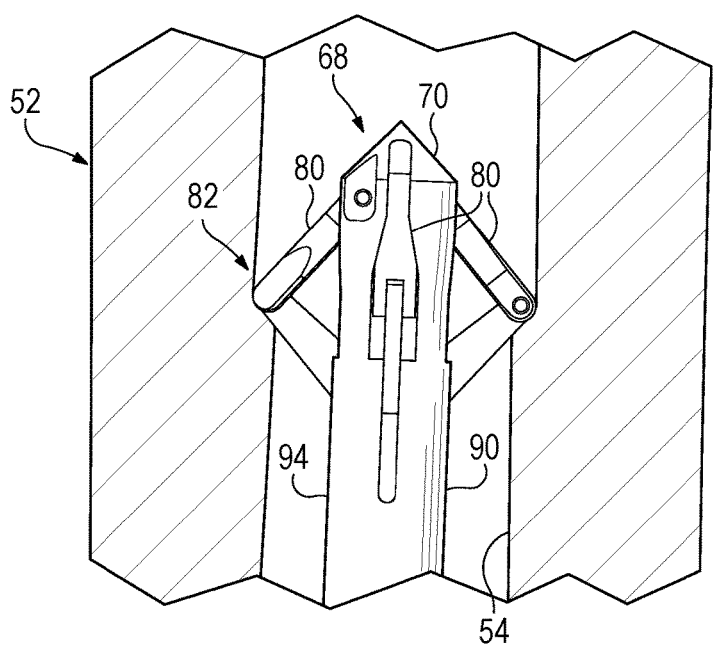

Rotation of inner member 114 may be coupled to rotation of user interface 74 and gauge screw 104 proximally (see FIGS. 4, 5, and 11). The cross-sectional shape of inner member 114 may be circular distally. Proximally, the cross-sectional shape of inner member 114 may be non-circular and at least generally complementary to the cross-sectional shape of respective apertures 120, 122 extending axially through user interface 74 and gauge screw 104 (see FIG. 5). For example, inner member 114 may have at least one flat 124 that contacts a corresponding flat region of apertures 120, 122. Accordingly, one revolution of user interface 74 drives one revolution of inner member 114, which drives one revolution of gauge screw 104. Therefore, the current axial position of gauge screw 104, shown by an index 126, corresponds to the current diameter of cutting head 68. A user can read the current diameter of cutting head 68 by comparing index 126 with at least one scale 128 arranged along a proximal section of shaft 56 (e.g., on opposite sides thereof in the depicted embodiment; see FIG. 11). Index 126 may be pivotably coupled to a nonthreaded region of gauge screw 104, at a fixed position along the gauge screw, such that the index travels axially with gauge screw 104. Each scale 128 may have a series of indicia that represent different diameters of cutting head 68. The indicia may, for example, include characters (letters, numbers, or other symbols), marks or areas of different color to color-code diameters, or the like.

User interface 74 and gauge screw 104 each may be slidably coupled to inner member 114, to permit axial movement of these components relative to one another. This ability for relative axial movement allows the external threads of gauge screw 104 and inner member 114 to have a different pitch from one another, and permits the proximal end of the inner member to move with respect to the proximal end of shaft 56 during reaming, in order to accommodate axial and rotational slop of the shaft.

Shaft 56 may have a body member 130 forming proximal portion 64 (see FIGS. 4, 5, and 11). The body member may be firmly attached to the proximal end of sleeve 84. User interface 74 may be located at least partially in an opening 132 defined by body member 130. Body member 130 also may define a pair of axial slots 134 adjacent internal thread 106, for axial travel of index 126 driven by rotation of user interface 74.

User interface 74 may form an incrementally adjustable, toothed interface 136 with proximal portion 64 of shaft 56 (see FIG. 5). The toothed interface, interchangeably termed a ratchet, may discourage unwanted rotation of user interface 74 with respect to shaft 56, by increasing the resistance to rotation of user interface 74. Alternatively, or in addition, toothed interface 136 may produce aural/haptic feedback, such as clicking and/or varying resistance, to the user as the diameter of the cutting head is being adjusted. Toothed interface 136 may be created by a set of radial teeth 138 on the end of user interface 74 that mesh with corresponding teeth 140 of an insert 142 fixed to body member 130 (see FIGS. 4 and 5). A spring 143 may be located in opening 132 of body member 130, between knob 76 and an inner wall of body member 130. The spring maintains engagement between the sets of teeth of toothed interface 136, to avoid unintended changes to the size of the cutting head.

Exemplary features of graspable member 60 are shown in FIGS. 4, 5, 6, and 11. Graspable member 60 may encircle, and optionally enclose, a section of shaft 56. In the depicted embodiment, graspable member 60 radially surrounds a leading end section of body member 130 and a trailing end section of sleeve 84. Graspable member 60, and optionally a handle portion thereof, is rotatable about the shaft. The graspable member and/or handle portion may or may not be slidable axially along the shaft, too. Embodiments that permit the graspable member and/or handle portion to slide axially may not supply irrigation fluid to the shaft via the graspable member and/or handle portion.

Graspable member 60 may have a port 144, which may be configured to receive irrigation fluid from a source thereof (see FIG. 4). A channel 146 may direct the irrigation fluid from port 144 to a chamber 148 encircling a section of body member 130 (see FIG. 5). Body member 130 may define an inlet 150 for flow of the irrigation fluid from chamber 148 to longitudinal channel 86 of sleeve 84. A fluid-tight seal may be formed between a section of body member 130 and graspable member 60. For example, a pair of ring gaskets 152 may encircle the section of the body member. A flat gasket may seal the junction between a base 154 and a cap 156 of graspable member 60. Another gasket 158 may prevent fluid leakage around a brake 160 configured to be pressed to slow or stop rotation of shaft 56. The irrigation fluid may flow along channel 86, in a space between the wall of channel 86 and inner member 114, to at least one outlet 161 defined by distal end region 94 of shaft 56 (see FIG. 6). The irrigation fluid leaves the shaft at outlet(s) 161.

Graspable member 60 may be configured to be gripped about any suitable axis or axes (see FIG. 4). A user's hand may grasp member 60 generally about long axis 58 defined by shaft 56, or an axis parallel to the long axis, at an encircling portion 162. In some embodiments, graspable member 60 may form a graspable handle portion 164, which may be attached to encircling portion 162. Handle portion 164 may be elongated transverse to long axis 58 along a handle axis 166. The handle axis may, for example, be within about 20 or 30 degrees, among others, of orthogonal to long axis 58. The handle portion may be configured to be grasped about handle axis 166. In some embodiments, handle portion 164 may define a plurality of depressions 168 arranged along handle axis 166 and each configured to receive at least a portion of a user's finger.

Figure 7:
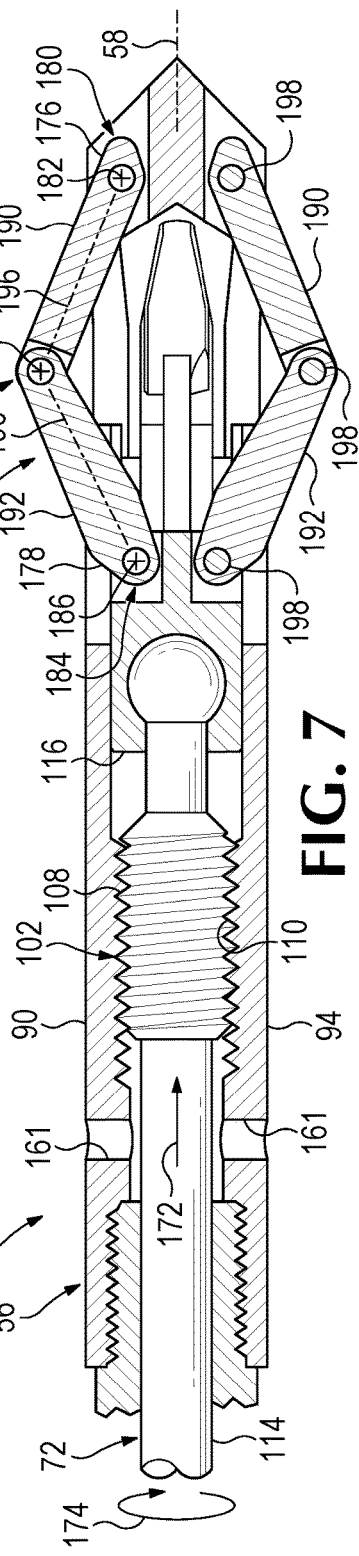
Figure 8:
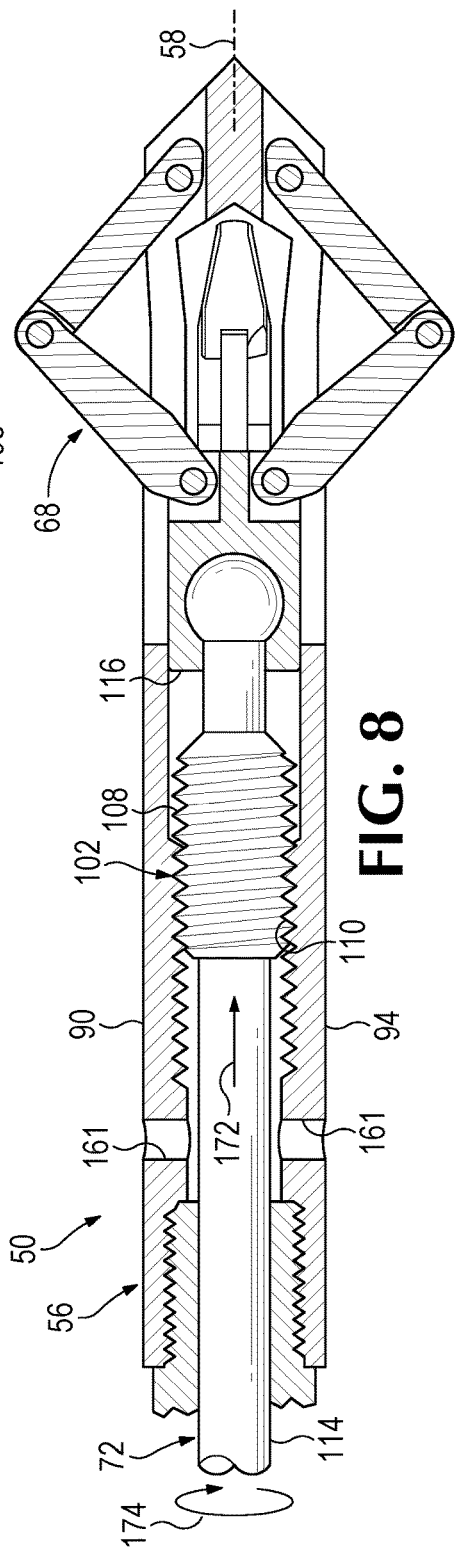

FIGS. 6-8 respectively show cutting head 68 of reamer 50 in fully-contracted, partially-expanded, and fully-expanded configurations. The fully-contracted configuration of FIG. 6 may (or may not) be a substantially non-cutting configuration in which cutting members 80 do not extend farther from long axis 58 than the radius of shaft 56 in distal end region 94. The expanded configurations of FIGS. 7 and 8 may position part of each cutting member 80, and particularly a cutting edge 170 thereof (see FIG. 9), farther from long axis 58 than the radius of shaft 56, such that cutting edge 170 can cut bone when the reamer is operated.

Cutting edge 170 may have any suitable structure. The cutting edge may be created at least in part by a depression 171 formed in a side of cutting member 80. Cutting edge 170 may result from a pair of surface regions that meet one another at an included acute angle, such as an acute angle of less than about 80, 70, 60, or 50 degrees, among others.

FIGS. 7 and 8, when compared with FIG. 6 and one another, illustrate how threaded travel of inner member 114 along distal end region 94 of shaft 56 changes the diameter of cutting head 68. External thread 108 of inner member 114 has a more proximal position in distal threaded connection 102 in FIG. 6 relative to FIGS. 7 and 8. The external thread is advanced distally, indicated by motion arrows 172, by rotation of inner member 114, indicated by rotation arrows 174 (see FIGS. 7 and 8). This threaded advancement of inner member 114 may drive axial motion (e.g., translational motion) of carriage 116 along long axis 58.

Each cutting member 80 may be elongated between a leading end 176 and a trailing end 178 (interchangeably called a distal end and a proximal end, respectively) (see FIG. 7). One of the ends (e.g., leading end 176) may be pivotably connected to distal end region 94 of shaft 56 at a joint (e.g., a leading joint 180) for rotation about a pivot axis 182. The other end (e.g., trailing end 178) may be pivotably connected to carriage 116 at a joint (e.g., a trailing joint 184) for rotation about a pivot axis 186. Cutting member 80 further may have at least one intermediate joint 188 located along the cutting member between ends 176, 178 and between joints 180, 184. Intermediate joint 188 may pivotably connect a pair of segments of cutting member 80 to one another, such as a leading segment 190 and a trailing segment 192 for rotation about a pivot axis 194. Segments 190, 192 each may be elongated along a long axis 196 of cutting member 80, and may form leading end 176 and trailing end 178, respectively. Each joint may include a pivot pin 198 that pivotably connects one of segments 190, 192 to shaft 56, carriage 116, or the other segment 190, 192. In other embodiments, each cutting member may include three or more discrete segments that are pivotably connected to one another via two or more intermediate joints.

Intermediate joint 188 may be located radially outward of a line extending through the center of joints 180 and 184. Accordingly, the pivot axis of joint 188 may be farther from long axis 58 than the pivot axis of joint 180 and/or joint 184. This arrangement ensures that each cutting member flexes outward when compressed axially, even if the cutting member has a fully retracted configuration that is linear.

Cutting edge 170 may be formed on one or both segments 190, 192 (see FIG. 9). In the depicted embodiment, the cutting edge is formed only on leading segment 190, but extends past pivot axis 194 proximally on a path that curves at least partway around the pivot axis (see FIG. 9). Accordingly, leading segment 190 can cut bone whether the reamer is being advanced or retracted. Leading segment 190 may be thicker than trailing segment 192 (measured parallel to pivot axis 194), at least near intermediate joint 188. Leading segment 190 may have a forked end 200 defining a notch 201 to receive an end of trailing segment 192. In some embodiments, the orientation of cutting members 80 may be reversed, such that trailing segment 192 is thicker than leading segment 190, forms forked end 200, and/or includes cutting edge 170.

Distal end region 94 of shaft 56 may define longitudinal slots 202, with each cutting member 80 being at least partially located in a respective one of slots 202 (see FIGS. 4, 6, and 9). Each slot 202 provides a space into which the corresponding cutting member 80 can be retracted, and from which the cutting member can be deployed. The slot may be configured to buttress cutting member 80, and may have a width 204, measured tangentially (parallel to pivot axis 194), that matches a corresponding transverse dimension 206 (e.g., the local thickness) of the cutting member. Width 204 may or may not vary along the length of slot 202. Respective leading and trailing sections of slot 202 may match respective transverse dimensions 206 of leading segment 190 and trailing segment 192. These relationships may permit contact between one or both segments 190, 192 and at least one wall region 208 of slot 202, to stabilize cutting member 80 as the cutting member is cutting bone.

Reamer 50 may have an axial passage 209, shown in phantom in FIG. 6, extending through shaft 56 between opposite ends thereof. The axial passage may be sized to receive a guide wire, such that the reamer can be guided inside the medullary cavity by the guide wire. Passage 209 may be defined partially by shaft 56 and partially by actuator 72.

II. Methods of Reaming Bone

This section describes exemplary methods of reaming bone using a reamer having an expandable cutting head (e.g., reamer 50); see FIGS. 1, 2, and 12-15. The method steps described in this section may be performed in any suitable order and combination using a reamer having any suitable combination of components and features disclosed herein.

A bone 52 to be reamed may be selected. Any suitable bone may be selected, such as a long bone of the arm (a humerus, an ulna, or a radius) or the leg (a femur, tibia, or fibula). The medullary cavity of the bone may be accessed by forming a hole in the bone. The hole may be formed in general axial alignment with the medullary cavity, or may be formed off-axis (e.g., see FIG. 1).

A reaming device, such as reamer 50, may be selected. A cutting head 68 of the device may be placed into the medullary cavity via the hole. The cutting head may be expanded after entering the medullary cavity. This expansion may occur before or after the cutting head has been passed through the isthmus of the medullary cavity, or this expansion may occur when the cutting head has been positioned at the isthmus. The location of the cutting head with respect to the isthmus may be determined by radiographic imaging (e.g., fluoroscopy). In some embodiments, the cutting head may be expanded until the user feels resistance to further expansion, due to contact between the wall of the medullary cavity and one or more cutting members of the cutting head. A diameter of the cutting head (and thus a local diameter of the medullary cavity) then may be read from a gauge of the reamer. Alternatively, the user can use radiographic imaging to visualize when the cutting head has been expanded to the desired diameter.

Cutting head 68 may cut bone from the wall of medullary cavity 54 as cutting head 68 is spinning about a long axis of a shaft of the device. The cutting head may be pushed (push-reaming) or pulled (pull-reaming) to respectively advance or retract the cutting head as it reams bone. When the reamer has a flexible shaft as disclosed herein, pull-reaming may be more effective, as axial force may be transmitted more efficiently along the shaft under tension relative to compression. Pull-reaming also may be safer than push-reaming, as the intramedullary pressure may be significantly lower. After reaming the bone, the reamer may be removed and an intramedullary nail may be placed into the reamed medullary cavity. The nail may be attached to the bone with fasteners.

FIGS. 12-15 illustrate exemplary configurations produced during performance of a pull-reaming method. Cutting head 68 of reamer 50 may be placed into medullary cavity 54 of a bone, such as femur 52. The cutting head may be pushed, indicated by an arrow at 210 through an isthmus 212 (a narrowed region) of the medullary cavity (see FIG. 12). The cutting head may pass through the isthmus while in a relatively contracted configuration, as shown. In this configuration, the diameter of cutting head 68 may be less than the diameter of isthmus 212, such that the cutting head can pass through isthmus 212 without cutting bone (and without being rotated). Cutting head 68 may be advanced to a wider region 214 of the medullary cavity beyond isthmus 212 (see FIG. 13). Cutting head 68 may be expanded in wider region 214, indicated by arrows at 216. Expanded cutting head 68 may be pulled back through the isthmus, indicated by an arrow at 218, as the cutting head is rotating, indicated by a rotation arrow at 220 (see FIG. 14). Cutting head 68 may widen isthmus 212, indicated by an arrow at 222, as the cutting head is pulled through the isthmus (see FIGS. 14 and 15).

III. Selected Embodiments

This section describes selected embodiments of reamers having an expandable cutting head and methods of reaming bone using reamers having an expandable cutting head. The elements, features, and aspects of the reamers and reaming methods described in this section may be combined with one another and with any of the elements, features, and aspects of the reamers and reaming methods described elsewhere in the present disclosure, in any suitable combination. These embodiments are intended for illustration and should not limit the entire scope of the present disclosure.

Paragraph A1. A device for reaming bone, comprising: (i) a shaft configured to be rotated about a long axis thereof; (ii) a plurality of cutting members connected to a distal end region of the shaft, rotationally offset from one another about the long axis, and forming at least a portion of a cutting head; and (iii) an inner member, such as a rod, configured to be moved with respect to the shaft, to change a diameter of the cutting head.

Paragraph A2. The device of paragraph A1, wherein the inner member is disposed in threaded engagement with the distal end region of the shaft, and wherein the inner member is configured to be rotated about the long axis with the respect to the shaft, to change the diameter of the cutting head.

Paragraph A3. The device of paragraph A2, wherein the threaded engagement creates a distal threaded connection, further comprising a proximal threaded connection forming part of a gauge configured to indicate the diameter of the cutting head.

Paragraph A4. The device of paragraph A3, wherein the proximal threaded connection is formed by a threaded member disposed in threaded engagement with a proximal portion of the shaft, and wherein rotation of the inner member and rotation of the threaded member are coupled to one another.

Paragraph A5. The device of any of paragraphs A1 to A4, further comprising an actuator including the inner member and a graspable user interface, wherein the user interface is configured to be rotated manually to change the diameter of the cutting head.

Paragraph A6. The device of paragraph A5, wherein the inner member and the user interface are configured to be movable relative to one another along the long axis. Paragraph A7. The device of paragraph A5 or A6, wherein the user interface includes a graspable knob.

Paragraph A8. The device of any of paragraphs A1 to A7, wherein each cutting member has a first end pivotably connected to the shaft and a second end pivotably connected to a carriage, and wherein the carriage is configured to move translationally along the long axis of the shaft when the inner member is moved relative to the shaft.

Paragraph A9. The device of any of paragraphs A1 to A8, wherein each cutting member includes a first segment, a second segment, and a joint pivotably connecting the first and second segments to one another, and wherein the first and second segments are discrete from one another and the shaft.

Paragraph A10. The device of paragraph A9, wherein each cutting member has opposite ends, wherein the first segment extends to one of the opposite ends, and wherein the second segment extends to the other opposite end.

Paragraph A11. The device of paragraph A9 or A10, further comprising a carriage slidably coupled to the shaft, wherein the joint is a first joint, wherein the cutting member has opposite ends, wherein one of the opposite ends of the cutting member is pivotably connected to the shaft by a second joint, and wherein the other opposite end of the cutting member is pivotably connected to the carriage by a third joint.

Paragraph A12. The device of any of paragraphs A9 to A11, wherein the cutting member has a cutting edge formed by one of the first and second segments and extending at least partway around a pivot axis defined by the joint.

Paragraph A13. The device of paragraph A12, wherein at least part of the cutting edge forms a curved portion, and wherein the curved portion has a center of curvature on the pivot axis.

Paragraph A14. The device of any of paragraphs A9 to A13, wherein only one of the segments of each cutting member is configured to cut bone.

Paragraph A15. The device of any of paragraphs A9 to A14, wherein the first segment is pivotably connected to the shaft, and wherein the second segment is pivotably connected to a carriage configured to move translationally along the long axis of the shaft when the inner member is rotated about the long axis.

Paragraph A16. The device of any of paragraphs A9 to A15, wherein the joint defines a pivot axis, and wherein rotation of the inner member changes a distance between the pivot axis and the long axis of the shaft.

Paragraph A17. The device of any of paragraphs A9 to A16, wherein one of the segments has a forked end, and wherein an end of the other segment is located between branches of the forked end.

Paragraph A18. The device of any of paragraphs A1 to A17, wherein the shaft defines a plurality of longitudinal slots, and wherein each cutting member is at least partially located in one of the slots.

Paragraph A19. The device of paragraph A18, wherein the cutting member is configured to be buttressed by a wall of the one slot when the cutting head is reaming bone.

Paragraph A20. The device of paragraph A19, wherein each cutting member includes a pair of elongated segments pivotably connected to one another at a joint, and wherein each of the elongated segments is configured to be buttressed by a wall region of one of the slots when the cutting head is reaming bone.

Paragraph A21. The device of any of paragraphs A1 to A20, wherein the shaft includes a flexible sleeve extending along a majority of the length of the shaft.

Paragraph A22. The device of paragraph A21, wherein the distal end region of the shaft and at least a section of the flexible sleeve are formed integrally with one another.

Paragraph A23. The device of paragraph A21 or A22, wherein the distal end region of the shaft is formed by a distal support member that is discrete from, and less flexible than, the flexible sleeve, and wherein the distal support member forms a supporting portion of the cutting head.

Paragraph A24. The device of any of paragraphs A21 to A23, wherein the sleeve has a plurality of discrete sections arranged along the long axis and making the sleeve flexible.

Paragraph A25. The device of any of paragraphs A21 to 23, wherein the shaft has a slit that extends multiple times around the long axis and makes the sleeve flexible, wherein the sleeve has a lateral periphery and defines a longitudinal channel, and wherein the slit has a radial extent from the lateral periphery to the longitudinal channel Paragraph A26. The device of any of paragraphs A1 to A25, further comprising a graspable member disposed around a section of the shaft and configured to be held by a user as the shaft is rotated with respect to the graspable member about the long axis.

Paragraph A27. The device of paragraph A26, wherein the graspable member has a handle portion that is elongated along a handle axis transverse to the long axis.

Paragraph A28. The device of any of paragraphs A1 to A27, wherein the plurality of cutting members includes at least three cutting members.

Paragraph A29. The device of any of paragraphs A1 to A28, wherein the device defines an axial passage configured to permit a guide wire to extend along the long axis through the device, and wherein the axial passage extends longitudinally through the inner member.

Paragraph A30. The device of any of paragraphs A1 to A29, wherein the shaft forms part of the cutting head.

Paragraph A31. The device of any of paragraphs A1 to A30, wherein the inner member has a threaded connection to the shaft at a position proximal to the cutting head.

Paragraph B1. A device for reaming bone, comprising: (i) a graspable member; (ii) a shaft coupled to the graspable member and configured to rotate with respect to the graspable member about a long axis of the shaft; (iii) a plurality of cutting members connected to a distal end region of the shaft and rotationally offset from one another about the long axis, each cutting member having a first segment and a second segment pivotably connected to one another at a joint; and (iv) an inner member, such as a rod, extending along the long axis inside the shaft; wherein the inner member is configured to be moved with respect to the shaft such that a distance between the joint and the long axis of the shaft changes.

Paragraph B2. The device of paragraph B1, wherein the inner member is in threaded engagement with a distal end region of the shaft.

Paragraph B3. The device of paragraph B1 or B2, wherein each cutting member has opposite ends, wherein the first segment extends to one of the opposite ends, and wherein the second segment extends to the other opposite end.

Paragraph B4. The device of any of paragraphs B1 to B3, further comprising a carriage configured to move axially in the shaft, wherein the joint is a first joint, wherein the cutting member has opposite ends, wherein one of the opposite ends of the cutting member is pivotably connected to the shaft at a second joint, and wherein the other opposite end of the cutting member is pivotably connected to the carriage at a third joint.

Paragraph B5. The device of any of paragraphs B1 to B4, wherein the cutting member has a cutting edge formed by one of the first and second segments and extending at least partway around a pivot axis defined by the joint.

Paragraph B6. The device of paragraph B5, wherein at least part of the cutting edge forms a curved portion, and wherein the curved portion has a center of curvature on the pivot axis.

Paragraph B7. The device of any of paragraphs B1 to B6, further including any limitation of combination of limitations from paragraphs A1 to A31.

Paragraph C1. A device for reaming bone, comprising: (i) a shaft configured to be rotated about a long axis of the shaft, the shaft including a flexible sleeve; (ii) a carriage configured to slide axially in the shaft; (iii) a plurality of cutting members connected to a distal end region of the shaft and rotationally offset from one another about the long axis, each cutting member having a first segment and a second segment pivotably connected to one another at a joint, wherein one end of the cutting member is pivotably connected to the shaft and an opposite end of the cutting member is pivotably connected to the carriage; and (iv) an inner member, such as a rod, extending longitudinally in the sleeve and connected to the carriage; wherein the cutting members form at least a portion of a cutting head, and wherein the inner member is configured to be moved with respect to the shaft to drive motion of the carriage along the long axis, such that a diameter of the cutting head changes.

Paragraph C2. The device of paragraph C1, wherein the inner member is configured to be rotated with respect to the shaft to drive motion of the carriage along the long axis.

Paragraph C3. The device of paragraph C1 or C2, wherein the shaft defines a plurality of longitudinal slots, and wherein each cutting member is at least partially located in one of the slots.

Paragraph C4. The device of paragraph C3, wherein the cutting member is configured to be buttressed by a wall of the one slot when the cutting head is reaming bone.

Paragraph C5. The device of any of paragraphs C1 to C4, wherein only one of the segments of each cutting member is configured to cut bone.

Paragraph C6. The device of any of paragraphs C1 to C5, wherein the joint is configured to move farther from the long axis when the diameter of the cutting head is increased by moving the inner member with respect to the shaft.

Paragraph C7. The device of any of paragraphs C1 to C6, further including any limitation or combination of limitations from paragraphs A1 to A31 and B1 to B6.

Paragraph D1. A method of reaming bone, the method comprising: reaming bone with the device of any of paragraphs A1 to A31, B1 to B7, and C1 to C7.

Paragraph D2. The method of paragraph D1, further comprising a step of inserting the cutting head into a medullary cavity of a long bone, wherein the step of reaming includes a step of removing bone material from the wall of the medullary cavity.

Paragraph D3. The method of paragraph D1 or D2, further comprising a step of forming an opening in a bone to access the medullary cavity, wherein the step of reaming is performed with the cutting head having a diameter greater than the diameter of the opening in the bone.

Paragraph D4. The method of any of paragraphs D1 to D3, further comprising a step of expanding the cutting head inside the medullary cavity before the step of reaming, a step of contracting the cutting head inside the medullary cavity after the step of reaming, and a step of removing the cutting head from the medullary cavity via the opening after the step of contracting.

Paragraph E1. A method of reaming a bone, the method comprising, in any order: (i) placing a cutting head of a reamer into a medullary cavity of a bone; (ii) advancing the cutting head through a narrower region to a wider region of the medullary cavity; (iii) expanding the cutting head in the wider region; and (iv) pulling the expanded cutting head back through the narrower region as the cutting head is rotating, such that the cutting head widens the narrower region.

Paragraph E2. The method of paragraph E1, wherein step of advancing is performed while the diameter of the cutting head is less than a diameter of the narrower region.

Paragraph E3. The method of paragraph E1 or paragraph E2, wherein the step of advancing includes a step of pushing the cutting head through the narrower region while the cutting head is not spinning.

Paragraph E4. The method of any of paragraphs E1 to E3, wherein the bone is a long bone and the narrower region is the isthmus of the medullary cavity.

Paragraph E5. The method of paragraph E4, further comprising a step of forming an opening in the bone to access the medullary cavity, wherein the opening defines a through-axis that is offset from parallel to a long axis of the medullary cavity by at least about 20, 30, or 40 degrees.

Paragraph E6. The method of paragraph E5, further comprising a step of bending a shaft of the reamer such that respective portions of the shaft extend along the through-axis of the opening in the bone and the long axis of the medullary cavity.

Paragraph E7. The method of any of paragraphs E1 to E6, wherein the step of expanding includes a step of rotating a user interface outside the bone.

Paragraph E8. The method of any of paragraphs E1 to E7, performed with the device of any of paragraphs A1 to A31, B1 to B7, and C1 to C7 Paragraph E9. The method of any of paragraphs E1 to E8, further comprising any step(s) and/or limitation(s) of paragraphs D1 to D4.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure. Further, ordinal indicators, such as first, second, or third, for identified elements are used to distinguish between the elements, and do not indicate a particular position or order of such elements, unless otherwise specifically stated.

We claim:

1. A method of reaming bone comprising:
placing a cutting head of a reaming device into a hole formed in a medullary cavity of a bone when the cutting head is in a contracted state;
advancing the contracted cutting head through a narrower region of the medullary cavity to a wider region of the medullary cavity;
expanding the contracted cutting head to an expanded state when the contracted cutting head is in the wider region; and
pulling the expanded cutting head back through the narrower region while the expanded cutting head is rotating thereby widening the narrower region via the expanded cutting head,
wherein the reaming device includes:
a shaft configured to be rotated about a long axis thereof, the shaft including a body portion and an elongate portion extending from the body portion, and
an actuator disposed within the shaft and rotatable relative to the shaft, the actuator including a knob disposed within the body portion and an inner member at least partially disposed within the elongate portion.

2. The method of claim 1, further comprising contracting the expanded cutting head back to the contracted state subsequent to widening the narrower region and removing the contracted cutting head from the medullary cavity.

3. The method of claim 1, further comprising removing the expanded cutting head from the medullary cavity subsequent to widening the narrower region.

4. The method of claim 1, wherein the wider region of the medullary cavity is located in cortical bone.

5. The method of claim 1, wherein the bone is a femur, tibia, fibula, talus, calcaneus, humerus, ulna, or radius bone.

6. The method of claim 1, wherein the hole formed in the medullary cavity is in axial alignment with the medullary cavity.

7. The method of claim 1, wherein the narrower region of the medullary cavity comprises an isthmus, wherein the contracted cutting head is expanded subsequent to the contracted cutting head being advanced through the isthmus of the medullary cavity.

8. The method of claim 1, further comprising determining a position of the contracted cutting head within the medullary cavity via radiographic imaging prior to expanding the contracted cutting head.

9. The method of claim 1, further comprising determining the contracted cutting head is expanded to a desired size in the expanded state via a gauge of the reaming device.

10. The method of claim 1, further comprising determining the contracted cutting head is expanded to a desired size in the expanded state via radiographic imaging.

11. The method of claim 1, wherein the contracted cutting head is expanded until resistance to further expansion is encountered as a result of contact between one or more cutting members of the cutting head and the medullary cavity.

12. The method of claim 1, wherein the shaft comprises a flexible shaft leading to the cutting head.

13. The method of claim 1, wherein the knob includes a first side opposite a second side, the first side of the knob including a first set of teeth, wherein the reaming device further includes a second set of teeth disposed in the body potion of the shaft configured to interface with the first set of teeth.

14. The method of claim 13, wherein the reaming device further includes a spring disposed in the body potion of the shaft such that the spring applies a force to the second side of the knob to thereby maintain contact between the first set of teeth of the knob and the second set of teeth.

15. The method of claim 1, wherein the cutting head of the reaming device includes a plurality of cutting members, each cutting member including a first segment and a second segment, wherein the first segment is pivotably coupled to the second segment at a joint, and wherein each cutting member has a cutting edge formed by at least one of the first and second segments and extending at least partway around the joint.

16. The method of claim 1, further comprising
rotating the inner member relative to the shaft to expand the contracted cutting head, and
rotating the shaft to rotate the expanded cutting head.

17. The method of claim 1, wherein a portion of the inner member is in threaded engagement with the shaft.

18. The method of claim 1, wherein the cutting head comprises a carriage, and the inner member and the carriage of the cutting form a spherical interface, which allows the inner member to rotate about the long axis with respect to the carriage.

19. The method of claim 18, wherein a rotation of the inner member relative to the shaft causes a translational motion of the carriage along the long axis, which changes a degree of deployment of cutting members and a diameter of the cutting head.

20. The method of claim 1, wherein the reaming device comprises an axial passage extending through the shaft between opposite ends thereof, wherein the axial passage is sized to receive a guide wire that is configured to guide the reaming device inside the medullary cavity.

* * * * *